United States Patent [19]

Mignani et al.

[11] Patent Number: 4,693,849
[45] Date of Patent: Sep. 15, 1987

[54] PREPARATION OF UNSATURATED COMPOUNDS

[75] Inventors: Gerard Mignani, Lyons; Didier Morel, Villiers sur Orge, both of France

[73] Assignee: Rhone-Poulenc Sante, Courbevoie, France

[21] Appl. No.: 775,835

[22] Filed: Sep. 13, 1985

Related U.S. Application Data

[62] Division of Ser. No. 671,963, Nov. 16, 1984, Pat. No. 4,615,838.

[30] Foreign Application Priority Data

Nov. 18, 1983 [FR] France ................................ 83 18392

[51] Int. Cl.$^4$ ..................... C09F 5/00; C07C 67/00; C07C 51/353; C07C 120/00
[52] U.S. Cl. ................................. 260/404; 260/405; 260/405.5; 260/410.9 R; 558/377; 558/440; 558/441; 558/442; 560/201; 560/205; 562/590; 562/598
[58] Field of Search .................... 260/404, 405, 405.5, 260/410.9 R; 560/201, 205; 562/590, 598; 558/440, 441, 442, 377

[56] References Cited

U.S. PATENT DOCUMENTS 4,564,477  1/1986  Takigawa et al. ............... 260/405.5

Primary Examiner—Werren B. Lone
Assistant Examiner—Vera C. Clarke
Attorney, Agent, or Firm—Stevens, Davis, Miller & Mosher

[57] ABSTRACT

Unsaturated compounds of the formula:

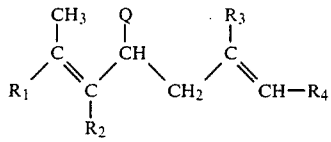

in which: Q denotes alkyloxycarbonyl, cyano or formyl, $R_1$ denotes a saturated or unsaturated aliphatic radical, $R_2$ denotes a hydrogen atom or an alkyl radical, $R_3$ denotes a hydrogen atom or an aliphatic radical and $R_4$ denotes a hydrogen atom or a saturated or unsaturated aliphatic radical which may be substituted, are useful as intermediates in the synthesis of vitamin E.

7 Claims, No Drawings

PREPARATION OF UNSATURATED COMPOUNDS

This is a division of application Ser. No. 671,963, filed Nov. 16, 1984, now U.S. Pat. No. 4,615,838.

The present invention provides new unsaturated compounds of the formula:

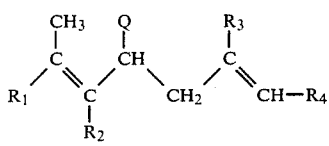

(I)

in which Q denotes alkyloxycarbonyl in which the alkyl has 1 to 4 carbon atoms as a straight or branched chain, carboxy, cyano or formyl;

$R_1$ denotes a saturated aliphatic radical of 1 to 11 carbon atoms or an unsaturated aliphatic radical of 2 to 11 carbon atoms and one or more double bonds;

$R_2$ denotes a hydrogen atom or alkyl radical of 1 to 4 carbon atoms;

$R_3$ denotes hydrogen or a saturated aliphatic radical of 1 to 11 carbon atoms; and $R_4$ denotes hydrogen, a saturated aliphatic radical of 1 to 11 carbon atoms, which is unsubstituted or substituted by acetyl, formyl which may be in the form of an acetal radical, hydroxy, which may be in the form of an ether or ester, or an unsaturated aliphatic radical of 2 to 11 carbon atoms and one or more double bonds, which is unsubstituted or substituted by acetyl, formyl which may be in the form of an acetal radical, or hydroxy which may be in the form of an ether or ester.

These compounds are useful as intermediates in the synthesis of vitamins A and E.

Of very particular interest are the compounds of formula (I) in which Q denotes alkyloxycarbonyl in which the alkyl has 1 to 4 carbon atoms, $R_1$ denotes an alkenyl radical containing 3 to 6 carbon atoms, $R_2$ denotes a hydrogen atom, $R_3$ denotes a methyl radical, and $R_4$ denotes a saturated aliphatic radical of 1 to 11 carbon atoms which is unsubstituted or substituted by acetyl, formyl which may be in the form of an acetal radical, or hydroxy which may be in the form of an ether or ester, or an unsaturated aliphatic radical of 2 to 11 carbon atoms and one or more double bonds, and more particularly two double bonds in the 1,3-position, which is unsubstituted or substituted by acetyl, formyl which may be in the form of an acetal radical, or hydroxy which may be in the form of an ether or ester.

Preferably, the unsaturated aliphatic radicals have an isoprenic or polyisoprenic structure.

According to a feature of the present invention, the unsaturated compounds of formula (I) are prepared by reaction of a compound of the formula:

$$X-CH_2-\overset{R_3}{\underset{}{C}}=CH-R_4 \quad (II)$$

or

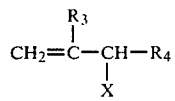

(III)

in which $R_3$ and $R_4$ are as defined above and X denotes halogen, methanesulphonyloxy, phenylsulphonyloxy, p-toluenesulphonyloxy or acetoxy, with a carbanion of the formula:

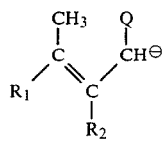

(IV)

in which Q, $R_1$ and $R_2$ are as defined above. This carbanion may be obtained by anionisation of a compound of the formula:

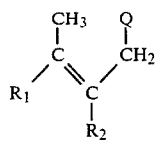

(V)

or

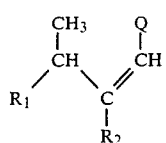

(VI)

in which Q, $R_1$ and $R_2$ are as defined above. The anionisation of a compound of formula (VI) is accompanied by a rearrangement leading to the carbanion of formula (IV).

The anionisation of a compound of the formula (V) or (VI) is advantageously carried out with a base such as an alcoholate, an amide, a hydride or a metal hydroxide, in the presence or absence of a quaternary ammonium salt. It is of particular interest to employ an alkali metal or alkaline earth tert-butylate, an alkali metal amide (e.g. alkali metal diisopropylamide) or tetrabutylammonium hydroxide. The anionisation may be carried out by operating in an organic solvent such as an ether, for example tetrahydrofuran, an aliphatic hydrocarbon, for example pentane, an aromatic hydrocarbon, for example toluene, or a polar aprotic solvent whose dielectric constant is low, for example dimethylformamide or N-methylpyrrolidone, at a temperature of between $-70°$ and $+50°$ C.

When use is made of a compound of formula (V) or (VI) in which Q denotes a carboxyl radical, it is necessary to employ a quantity of anionising agent which is twice the theoretical quantity.

The reaction of a compound of formula (II) or (III) with the carbanion of formula (IV) is preferably carried out in the presence of a catalyst based on palladium combined with a ligand, operating in a nonpolar organic solvent such as an aliphatic hydrocarbon, e.g. pentane, an aromatic hydrocarbon, e.g. toluene, or a chlorinated solvent, e.g. chloroform, at a temperature of between $-70°$ and $+100°$ C., and preferably between $0°$ and $30°$ C.

Suitable palladium-based catalysts which may be employed are derivatives of divalent palladium or complexes of palladium (O). Particularly suitable derivatives of divalent palladium are $PdCl_2$, $Pd(OCOCH_3)_2$, $Pd(NO_3)_2$, Pd (acetyl-acetonate)$_2$, $pdCl_2[P(C_6H_5)_3]_2$, $PdCl_2(PhCN)_2$, $PdCl_2(CH_3CN)_2$, $(C_3H_5PdCl)_2$, $(C_3H_5PdOCOCH_3)_2$, and $(C_3H_5)_2Pd$. Particularly suitable derivatives of palladium (O) are derivatives of the type $PdL_4$ in which L denotes a ligand chosen from phosphines, diphosphines, phosphites, arsines and stibines.

As ligands combined with palladium derivatives, derivatives of phosphorus, of antimony and of arsenic such as phosphines, arsines or stibines, are particularly suitable.

When the reaction is carried out in the presence of a catalyst, the quantity of the catalyst employed generally represents 0.1 to 10 mole % of the ester of general formula (V) or (VI) employed.

It is advantageous to employ the ligand in a quantity such that the molar ratio ligand/palladium is between 1 and 10.

It is of particular interest to note that, when the compound of formula (II) or (III) incorporates 2 double bonds in the 1,3-position, the use of a catalyst based on palladium in the presence of a ligand makes it possible to carry out the reaction despite the presence of a 1,3-diene.

The reaction of a compound of general formula (III) with the carbanion of formula (IV) can theoretically produce either a Linear product of formula (I) in accordance with a mechanism similar to the $SN_2'$ type, or a branched product of formula:

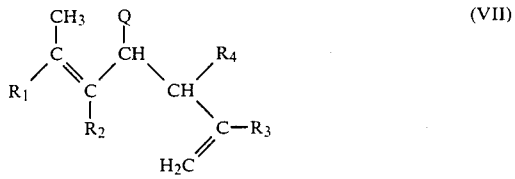

(VII)

in which Q, $R_1$, $R_2$, $R_3$ and $R_4$ are defined as above, in accordance with a mechanism similar to the $SN_2$ type.

Depending on the nature of the solvent employed, it is possible to direct the reaction preferentially towards the formation of a linear product of general formula (I) or a branched product of general formula (VII), the production of a linear product being generally carried out by operating in the presence of a catalyst such as defined above, in a nonpolar organic solvent.

Furthermore, the use of the palladium-based catalyst can sometimes result in an oxidation-reduction reaction in the region of the double bond of the anion of formula (IV) employed.

The compounds of formula (V) may be obtained from a 1,3-diene by hydrocarbonylation, by alkoxycarbonylation according to the process described in European Pat. No. 60,737, by hydrocyanation according to the process described in French Pat. No. 2,069,411, or by hydroformylation according to the process described in French Pat. No. 2,349,562.

The products of general formula (VI) may be obtained by a Knoevenagel reaction between aldehydes and compounds containing an active methylene group, according to the methods described in Organic Reactions, Volume 15, pages 205–273 (1967).

The compounds of formula (I) are particularly useful intermediates in the synthesis of vitamin E. Of particular interest are the compounds of formula (I) containing a 1,3-diene structure.

In a general manner, the conversion of the compounds of formula (I) consists in replacing, if need be, the radical Q by a carboxy radical and then hydrogenating and decarboxylating the product obtained to form a unit which is conventionally employed in the synthesis of vitamin E, such as phytone or geranylacetone.

When the radical Q denotes a cyano radical, hydrolysis of the nitrile function to an acid function may be carried out in accordance with the procedure described by Compagnon and Miocque, Ann. Chim. (Paris), [14]5, 11–27 (1970).

When the radical Q denotes a formyl radical, oxidation of the aldehyde function to an acid function may be carried out according to the procedure described by Chinn, "Selection of oxidants in synthesis", pages 63–70 (1971).

When the radical Q denotes a formyl radical, it is possible to replace the aldehyde function by a hydrogen atom, without passing through an acid function as an intermediate, by carrying out a decarbonylation reaction according to the procedure described by L. H. Pignolet, J. Amer. Chem. Soc., 100, 7083 (1978).

For example, the condensation of an ester of 4-methyl-3-pentenoic acid with 6-chloro-3-methylene-7-methyl-1,7-octadiene leads to a tetraene ester of general formula:

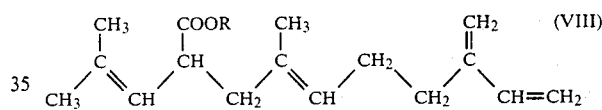

(VIII)

in which R denotes an alkyl radical containing 1 to 4 carbon atoms as a straight or branched chain or a hydrogen atom, which is converted to phytone after reaction, for example, with methyl acetylacetate, under the conditions described in European Pat. No. 44,771, followed by decarboxylation and hydrogenation of the product thus obtained, the decarboxylation being capable of being carried out before or after the hydrogenation.

The decarboxylation followed by hydrogenation may both be carried out for example under the conditions described by R. T. Arnold et al., J. Amer. Chem. Soc., 72 4359 (1950) while the hydrogenation followed by decarboxylation may be carried out for example under the conditions described by T. S. Oakwood and M. R. Miller, J. Amer. Chem. Soc., 72, 1849 (1950) or those described in U.S. Pat. No. 3,530,198.

Phytone obtained in this way may be converted to vitamin E by passing through isophytol as an intermediate according to the process described in Helvetica Chimica Acta, 21, 520–525 and 820–825 (1938).

The following Examples illustrate the invention.

EXAMPLE 1

Into a 100 cc round flask, under an argon atmosphere, are introduced dry pentane (10 cc) and diisopropylamine (2.07 g; 20 millimoles). After cooling to 0° C. a 1.6 mole/liter solution of n-butyllithium in hexene (12.5 cc; 20 millimoles) is added. The mixture is left to react for 20 minutes at 0° C., and then cooled to −78° C. Ethyl 4-methyl-3-pentenoate (2.78 g; 20 millimoles) is added slowly, then left to react for 20 minutes at −78° C., and then for 1 hour at a temperature of about 20° C.

Into a second 100 cc round flask, under an argon atmosphere, are introduced [C$_3$H$_5$PdCl]$_2$ (40 mg; 0.1 millimole), P(C$_6$H$_5$)$_3$ (2.30 mg; 0.87 millimole), dry toluene (5 cc) and 6-chloro-3-methylene-7-methyl-1,7-octadiene (3.5 g; 20 millimoles).

Into this last flask, the solution present in the first flask is introduced with the aid of a transfer needle; this operation is carried out over 20 minutes, and the reaction is then left to proceed for 2 hours at a temperature of about 20° C. The solution changes from light yellow to orange in colour. The reaction mass is poured into a 10% hydrochloric acid solution (30 cc). The aqueous phase separated by decantation is extracted with ether. The organic phases are combined and dried over magnesium sulphate. After filtration and evaporation of the solvent, a yellow oil (5.08 g) is obtained. After distillation under reduced pressure (T=111°-118° C. under 1.4 mm Hg; 0.18 kPa), a mixture (4.5 g) of products 1 and 2:

1:
(CH$_3$)$_2$C=CH—CH(CO$_2$C$_2$H$_5$)—CH$_2$—C(CH$_3$)=CH—CH$_2$—CH$_2$—C(=CH$_2$)—CH=CH$_2$

2:
(CH$_2$=C(CH$_3$)—CH[—CH(CO$_2$C$_2$H$_5$)—CH=C(CH$_3$)$_2$]—CH$_2$—CH$_2$—C(=CH$_2$)—CH=CH$_2$ is obtained.

The yield is 81.5%.

Analysis by gas phase chromatography shows a ratio 1/(1+2)=98%.

The structure of the products obtained is confirmed by the infrared spectrum, mass spectrum and the proton nuclear magnetic resonance spectrum.

EXAMPLE 2

Diisopropylamine (2.744 g; 20 millimoles) and dry toluene (6 cc) are introduced into a 100 cc round flask, under an argon atmosphere, and are then cooled to 0° C. A 1.6 mole/liter solution of n-butyllithium in hexene (17.5 cc) is then added slowly. The mixture is left to react for 20 minutes and is then cooled to −78° C. Ethyl 4,8-dimethyl-3,7-nonadienoate (5.965 g; 28.4 millimoles) is then added and then the temperature is allowed to rise to 25° C.

Into a second 100 cc round flask, under an argon atmosphere, are introduced dry toluene (3 cc), (C$_3$H$_5$PdCl)$_2$ (613 mg; 1.67 millimoles), P(C$_6$H$_5$)$_3$ (982 mg; 3.74 millimoles) and 6-chloro-3-methylene-7-methyl-1,7-octadiene (5.068 g; 29.7 millimoles). The first solution obtained is then added to the second at a temperature of about 20° C. and is then left to react for 1 hour at 25° C. The solution changes from light yellow to dark orange in colour. The reaction mass is hydrolysed with a 10N aqueous solution of hydrochloric acid. It is extracted with ether (3×50 cc). The combined organic phases are dried over magnesium sulphate. After filtration and then evaporation over the solvent, a yellow oil (10.854 g) is obtained. After being left for 15 hours at 0° C., a precipitate is formed, which is separated by filtration. An orange-coloured filtrate (9.097 g) is recovered.

Using high-pressure liquid chromatography (two SiO$_2$ columns; eluent: cyclohexane/dichloromethane: 4/3), the product of formula:

(CH$_3$)$_2$C=CH—CH$_2$—CH$_2$—C(CH$_3$)=CH—CH(CO$_2$C$_2$H$_5$)—CH$_2$—C(CH$_3$)=CH—CH$_2$—CH$_2$—C(=CH$_2$)—CH=CH$_2$ (2.7086 g) is obtained.

The yield is 28%.

Analysis of the crude reactoion product by gas phase chromatography shows that a single reaction product has been formed.

The structure of the product obtained is confirmed by mass spectrum, the proton nuclear magnetic resonance spectrum and the infrared spectrum.

EXAMPLE 3

Dry pentane (40 cc) and diisopropylamine (7 cc; 50.7 millimoles) are introduced into a 100 cc round flask, under an argon atmosphere. They are cooled to 0° C. and a 1.6 mole/liter solution of n-butyllithium in hexene (32 cc; 51.2 millimoles) is added. Reaction is left to proceed for 20 minutes at 0° C., and the mixture is then cooled to −78° C. Methyl 4-methyl-3-pentenoate (7.1 cc, 6.62 g; 51.7 millimoles) is then added, and then left to react at this temperature for 20 minutes and finally is allowed to return to the ambient temperature of 20° C.

Into a second 100 cc round flask, under an argon atmosphere, are introduced (C$_3$H$_5$PdCl)$_2$ (0.272 g; 1.49 milligram-atom of Pd), P(C$_6$H$_5$)$_3$ (1.61 g; 6.1 millimoles), dry toluene (30 cc) and 3-chloro-2-methylpropene (4.9 cc; 48.7 millimoles).

The first solution is introduced into the second with the aid of a transfer needle over 20 minutes. It is rinsed with dry toluene (10 cc) and then left to react for 12 hours at a temperature of about 20° C. The mixture is taken up in water and separated. The organic phase is dried over magnesium sulphate. After filtration and evaporation of the solvent a colourless oil (11.86 g) is obtained. After a distillation under reduced pressure (T=39°-40° C. under 0.3 mm Hg; 0.04 kPa), the product of formula:

(CH$_3$)$_2$C=CH—CH(CO$_2$CH$_3$)—CH$_2$—C(=CH$_2$)—CH$_3$ (5.52 g) is obtained.

The yield is 62%.

The structure of the product obtained is confirmed by the mass spectrum, the infrared spectrum and the proton nuclear magnetic resonance spectrum.

EXAMPLE 4

The procedure followed is the same as in Example 3, but using
methyl 4-methyl-3-pentenoate (6.4 g; 50 millimoles)
1-bromo-2-butene (6.7 g; 50 millimoles)
(C$_3$H$_5$PdCl)$_2$ (0.27 g; 1.49 milligram-atom of Pd)
P(C$_6$H$_5$)$_3$ (1.59 g; 6.1 millimoles)
A colourless oil (10.04 g) is obtained.
Distillation under reduced pressure (T=37°-39° C. under 0.2 mm Hg; 0.027 kPa) produces a mixture consisting of the product of formula:

(CH$_3$)$_2$C=CH—CH(CO$_2$CH$_3$)—CH$_2$—CH=CH—CH$_3$ (3.73 g; 40.9% yield) and the product of formula:

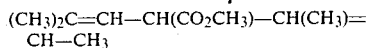
(CH$_3$)$_2$C=CH—CH(CO$_2$CH$_3$)—CH(CH$_3$)=CH—CH$_3$ (1.86 g; 20.4% yield).

The structure of the products is confirmed by the mass spectrum, the infrared spectrum and the proton nuclear magnetic resonance spectrum.

EXAMPLE 5

The procedure followed is the same as in Example 3, but using:
methyl 4-methyl-3-pentenoate (6.4 g; 50 millimoles)
CH$_3$—CHCl—CH=CH$_2$ (4.5 g; 50 millimoles)
(C$_3$H$_5$PdCl)$_2$ (0.27 g; 1.49 milligram-atom of Pd)
P(C$_6$H$_5$)$_3$ (1.59 g; 6.10 millimoles).

A colourless oil (10.05 g) is obtained.

Distillation under reduced pressure (T=52°–53° C. under 0.7 mm Hg; 0.093 kPa) produces a mixture consisting of the product of formula:

(CH$_3$)$_2$C=CH—CH(CO$_2$CH$_3$)—CH$_2$—CH=CH—CH$_3$ (2.194 g; 24.1% yield) and the product of formula:

(CH$_3$)$_2$C=CH—CH(CO$_2$CH$_3$)—CH(CH$_3$)—CH=CH$_2$ (1.223 g; 13.4% yield).

The structure of the products is confirmed by the mass spectrum, the infrared spectrum and the proton nuclear magnetic resonance spectrum.

EXAMPLE 6

Into a 100 cc round flask, under an argon atmosphere, are introduced finely ground caustic soda (0.56 g; 14 millimoles), tetrabutylammonium chloride (0.2 g) and dry toluene (30 cc). A mixture of ethyl 4-methyl-3-pentenoate (1.42 g; 10 millimoles) and 3-chloro-2-methylpropene (0.9 g; 10 millimoles) is then added over an hour. The reaction is left to proceed for 2 hours at a temperature of about 20° C. The heterogeneous solution is filtered, and is then taken up with water. The organic phase is dried over magnesium sulphate. After filtration and evaporation of the solvent, a pale yellow oil (2 g) is obtained, containing, according to analysis by gas phase chromatography, 85% of the product of formula:

(CH$_3$)$_2$C=CH—CH(CO$_2$C$_2$H$_5$)—CH$_2$—C(=CH$_2$)—CH$_3$

The yield is 93%.

The structure of the product obtained is confirmed by the mass spectrum, the proton nuclear magnetic resonance spectrum and the infrared spectrum.

EXAMPLE 7

The procedure followed is the same as in Example 3, but using:
methyl 3,4-dimethyl-3-pentenoate (7.1 g; 50 millimoles)
6-chloro-3-methylene-7-methyl-1,7-octadiene (8.5 g; 50 millimoles)
(C$_3$H$_5$PdCl)$_2$ (0.272 g; 1.49 milligram-atom of Pd)
P(C$_6$H$_5$)$_3$ (1.59 g; 6.1 millimoles).

After the usual treatment a yellow oil (18.91 g) is obtained which, after distillation under reduced pressure (T=108°–120° C. under 0.8 mm Hg; 0.11 kPa), gives: the product of formula:

(CH$_3$)$_2$C=C(CH$_3$)—CH(CO$_2$CH$_3$)—C(=O)—CH$_2$—C(CH$_3$)=C(CH$_3$)$_2$ (1.814 g; 14.4% yield) and the product of formula:

(CH$_3$)$_2$C=C(CH$_3$)—CH(CO$_2$CH$_3$)—CH$_2$—C(CH$_3$)=CH—CH$_2$—CH$_2$—C(=CH$_2$)—CH=CH$_2$ (3.309 g; 23.9% yield).

The structure of the products obtained is confirmed by the mass spectrum and the proton nuclear magnetic resonance spectrum.

EXAMPLE 8

Into a 100 cc three-necked round flask equipped with a reflux condenser and a thermometer, are introduced, at a temperature of about 20° C., the coupling product obtained in Example 1 (22.9 g i.e. 87.4 millimoles), [RhCl(1,5-cyclooctadiene)]$_2$ (0.0458 g; 0.186 milligram-atom of Rh), Na$_2$CO$_3$ (0.0847 g; 0.8 millimole), Na TPPTS (1.115 g), a 75-25 volume mixture of water and methanol (20 cc) and methyl acetylacetate (22.36 g; 192 millimoles). The reaction is left to proceed for 24 hours at 75° C. After the solution has cooled ether (100 cc) is added. After decantation, the organic phase is washed with water (3×30 cc). The solvent is evaporated off and then the solid obtained is taken up with pentane (100 cc). The organic phase is washed again with water (3×30 cc). The organic phases are combined and dried over magnesium sulphate. After filtration and evaporation of the solvent, a yellow oil (33.03 g) is obtained, which contains a mixture (30.97 g) of the products of formula:

(CH$_3$)$_2$C=CH—CH(CO$_2$CH$_3$)—CH$_2$—C(CH$_3$)=CH—CH$_2$—CH$_2$—C(CH$_3$)=CH—CH$_2$—CH(CO$_2$CH$_3$)—CO—CH$_3$ and (CH$_3$)$_2$C=CH—CH(CO$_2$CH$_3$)—CH$_2$—C(CH$_3$)=CH—CH$_2$—CH$_2$—C(=CH$_2$)—CH$_2$—CH$_2$—CH(CO$_2$CH$_3$)—CO—CH$_3$ The yield is 93.7%.

The structure of the products obtained is confirmed by the mass spectrum, the infrared spectrum and the proton nuclear magnetic resonance spectrum.

EXAMPLE 9

Into a 100 cc round flask are introduced the product obtained in Example 8 (29.95 g; 79.2 millimoles), a 30.75% solution of caustic soda (31 g; 0.238 mole of soda) and water (60 cc). The reaction is left to proceed for 1 hour at 40° C. until a homogeneous yellow solution is obtained, then 95% sulphuric acid (7 cc) and water (18 cc) are added. The reaction is left to proceed for 1 hour at 25° C. A vigorous release of carbon dioxide is observed. The solution obtained is extracted with ether (3×30 cc). The combined organic phases are dried over magnesium sulphate. After filtration and evaporation of the solvent, a mixture (23.19 g) of the products of formula:

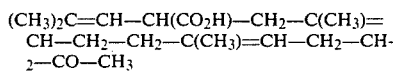

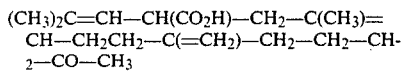

is obtained, in a 95% yield.

The structure of the products obtained is confirmed by the mass spectrum, the infrared spectrum and the proton nuclear magnetic resonance spectrum.

EXAMPLE 10

Into a 125 cc stainless steel autoclave are introduced, under an argon atmosphere, the product obtained in Example 9 (5 g; 16.3 millimoles), pentane (30 cc) and 10% Pd/C (0.2 g), followed by hydrogen to give a pressure of 100 bars. The reaction is left to proceed for 12 hours at a temperature of about 20° C. After filtration and then evaporation of the solvent, a colourless oil is obtained, which contains 98% of product of formula:

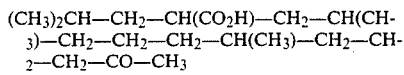

The structure of the product obtained is confirmed by the mass spectrum, the infrared spectrum and the proton and carbon 13 nuclear magnetic resonance spectra.

Heat treatment of the product obtained at a temperature of 150° C. results in phytone of formula:

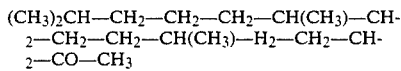

We claim:

1. A process for preparing an unsaturated compound of the formula:

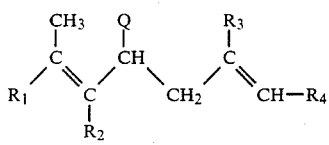

in which Q denotes alkyloxycarbonyl in which the alkyl has 1 to 4 carbon atoms as a straight or branched chain, carboxy, cyano or formyl;

$R_1$ denotes a saturated aliphatic radical of 1 to 11 carbon atoms or unsaturated aliphatic radical of 2 to 11 carbon atoms and one or more double bonds;

$R_2$ denotes hydrogen or an alkyl radical of 1 to 4 carbon atoms;

$R_3$ denoted hydrogen or a saturated aliphatic radical of 1 to 11 carbon atoms; and $R_4$ denotes hydrogen, a saturated aliphatic radical of 1 to 11 carbon atoms which is unsubstituted or substituted by acetyl, formyl which may be in the form of an acetal radical, hydroxy which may be in the form of an ether or ester, or an unsaturated aliphatic radical of 2 to 11 carbon atoms and one or more double bonds, which is unsubstituted or substituted by acetyl, formyl wich may be in the form of an acetal radical, or hydroxy which may be in the form of an ether or ester;

which comprises reacting a compound of the formula:

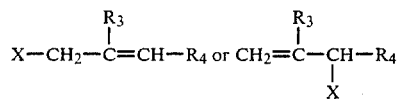

in which $R_3$ and $R_4$ are as defined above and X denotes halogen, methanesulphonyloxy, phenylsulphonyloxy, p-toluenesulphonyloxy or acetoxy, with a carbanion of the formula:

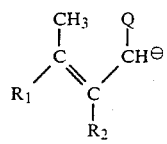

in which Q, $R_1$ and $R_2$ are defined above in the presence of a catalyst based on palladium combined with a ligand in a non-polar aprotic solvent at a temperature of between $-70°$ and $+100°$ C.

2. Process according to claim 1, in which the palladium-based catalyst is a derivative of divalent palladium or palladium (O).

3. Process according to claim 1, in which the ligand is a derivative of phosphorus, arsenic or antimony.

4. Process according to claim 8, in which the ligand is a phosphine, arsine or stibine.

5. Proces according to claim 1, in which the solvent is an aliphatic hydrocarbon, an aromatic hydrocarbon or a chlorinated solvent.

6. Process according to claim 1, in which the said catalyst is used in an amount between 0.1 and 10 mole % relative to the carbanion employed.

7. Process according to claim 1, in which the molar ratio ligand/palladium is from 1 to 10.

* * * * *